United States Patent [19]

Beckman et al.

[11] Patent Number: 4,995,403
[45] Date of Patent: Feb. 26, 1991

[54] PERIODONTAL PROBE

[75] Inventors: Ralph A. Beckman; Henry D. Sharpe, III, both of Providence; Len Curado, East Greenwich; James W. Barfoot, Providence, all of R.I.

[73] Assignee: Bausch & Lomb Professional Dental Products, Inc., Tucker, Ga.

[21] Appl. No.: 315,131

[22] Filed: Feb. 24, 1989

[51] Int. Cl.$^5$ .............................................. A61B 5/103
[52] U.S. Cl. ...................................... 128/776; 433/72; 433/118
[58] Field of Search ......................... 128/774, 776–777, 128/739, 740; 33/513–514; 433/33, 72, 115, 118, 120, 124

[56] References Cited

U.S. PATENT DOCUMENTS

| | | | |
|---|---|---|---|
| 3,943,914 | 3/1976 | Grenfell et al. | 128/776 |
| 4,182,312 | 1/1980 | Mushaback | 128/776 X |
| 4,677,756 | 7/1987 | Simon et al. | 128/776 X |
| 4,764,114 | 8/1988 | Jeffcoat et al. | 128/776 X |
| 4,791,940 | 12/1988 | Hirschfeld et al. | 128/776 |
| 4,823,809 | 4/1989 | Gott, Jr. et al. | 128/776 |

FOREIGN PATENT DOCUMENTS 0296520 12/1988 European Pat. Off. ............ 128/776

OTHER PUBLICATIONS

Van Der Velden et al., "Introd. of a New Periodontal Probe", Journal of Clin. Periodontology: 1978: 5: pp. 188–197.

Primary Examiner—Max Hindenburg
Assistant Examiner—John P. Lacyk
Attorney, Agent, or Firm—Salter & Michaelson

[57] ABSTRACT

A periodontal probe includes sequentially disposed, normally connected sensor, shaft and tip portions, and a longitudinally extending fiber element in the tip and shaft portions. The fiber element is retractable into the tip portion to measure the depths of periodontal pockets in the mouth of a patient, and the sensor portion is operative for generating electrical signals which cumulatively provide indications of the relative positions of the tip portion and the fiber element. The shaft portion, the tip portion and the fiber element are preferably disposable and detachably connected to the sensor portion so that they can be discarded after a single periodontal examination. The shaft portion and the tip portion preferably have a combined length of at least approximately 4½ inches so that only the disposable portions of the probe normally come into contact with the hands of a dentist or the mouth of a patient during a periodontal examination. The terminal end portion of the fiber element preferably has a series of different colored annular bands thereon so that a dentist can visually observe the position of the fiber element relative to the gingival margin during a periodontal examination.

17 Claims, 2 Drawing Sheets

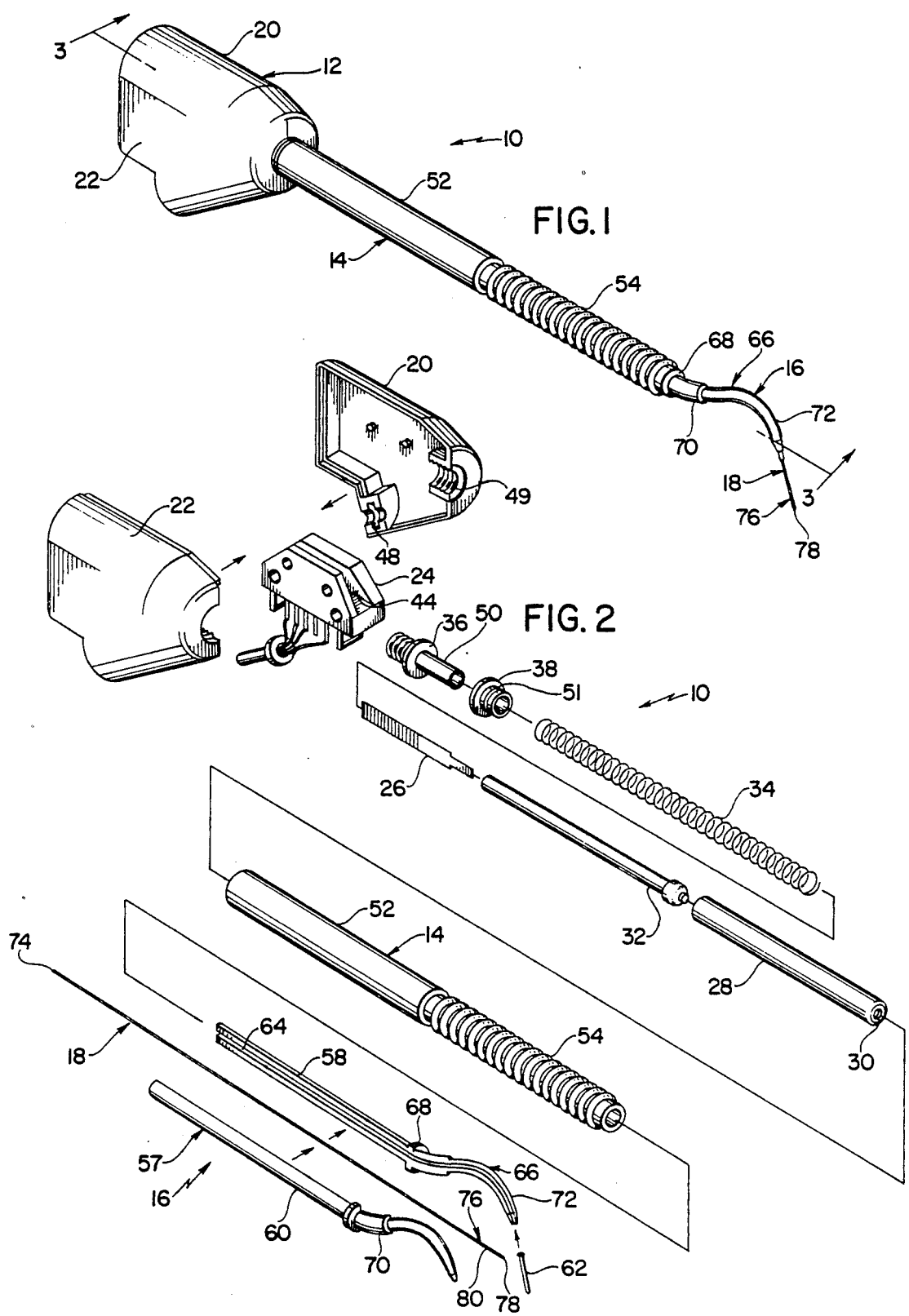

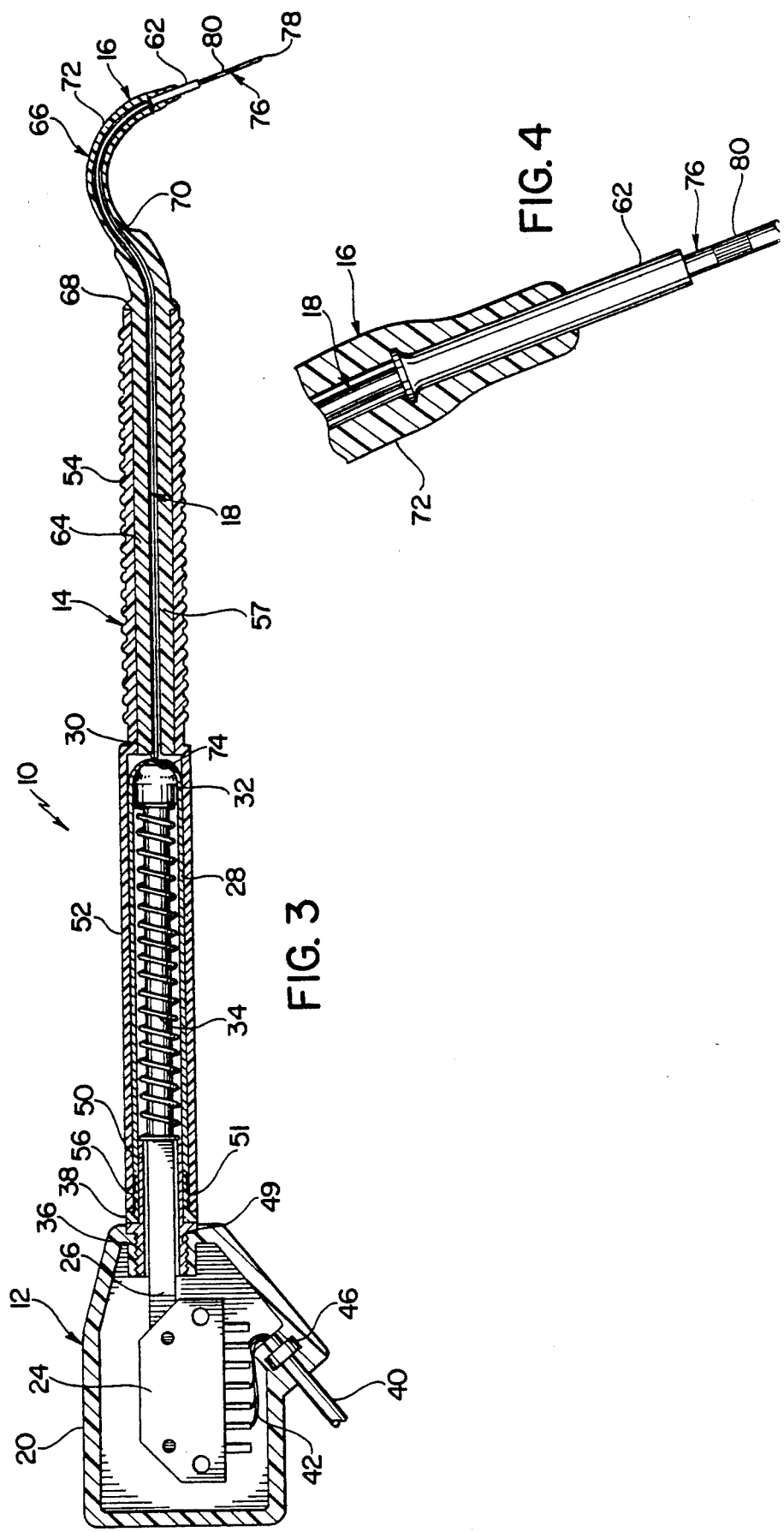

4,995,403

PERIODONTAL PROBE

BACKGROUND AND SUMMARY OF THE INVENTION

The instant invention relates to the field of dentistry and more particularly to a periodontal probe which is operable by a dentist for measuring the depths of the periodontal pockets in the gingival tissue in the mouth of a patient in order to monitor the progression of periodontal disease in the patient.

In recent years, periodontal disease has been recognized as one of the most widespread and serious dental afflictions encountered by dental patients. In this regard, it is well known in the dental field that periodontal disease is a progressive, plaque-induced affliction which can cause serious tissue inflammation, and therefore bone loss in the areas surrounding the teeth of patients. Further, it is generally known that in order to effectively treat periodontal disease, it is necessary to monitor the progression of the disease in the mouths of patients by monitoring gum recession, tissue condition and bone loss. Generally, this has been done by periodically visually examining the mouths of patients and by measuring the depths of any periodontal pockets in the gingival tissue surrounding the teeth therein. Originally, pocket depths were measured utilizing metal probes having calibration markings thereon. However, probes of this type were generally found to be awkward to use and manipulate in the mouths of patients, and they were often found to require time consuming measurement procedures which often produced results of questionable accuracy. More recently, however, more sophisticated electronic measuring probes having retractable tip portions have been developed which have been found to be capable of producing more accurate measurements of the depths of periodontal pockets in the mouths of patients. Devices of this type have generally been operable for generating electronic signals which are representative of periodontal pocket depths and for supplying these signals to various remote electronic recording and/or readout apparatus. Periodontal probes of this general type which represent the closest prior art to the subject invention of which the applicants are aware are disclosed in the U.S. patents to MOUSSEAU, U.S. Pat. No. 3,916,529; GRENFELL et al, U.S. Pat. No. 3,943,914; SUMPTION et al, U.S. Pat. No. 3,979,835; STARK et al, U.S. Pat. No. 4,164,214; ACKERMAN et al, U.S. Pat. No. 4,665,621; SIMON et al, U.S. Pat. No. 4,677,756; PIPPIN et al, U.S. Pat. No. 4,708,647; the Japanese Pat. application disclosure No. 59-40102 (1984) and the pending U.S. Pat. application to ACKERMAN et al, No. 07/024,991. However, these references fail to disclose or suggest a periodontal probe having many of the unique structural features and advantages of the periodontal probe of the subject invention, and hence they are believed to be of only general interest with respect thereto as will hereinafter be made apparent.

The periodontal probe of the instant invention comprises sequentially disposed, connected sensor, shaft and tip portions, and an elongated flexible fiber element which extends longitudinally through the tip portion and at least a portion of the shaft portion. The fiber element is assembled with the tip portion and the shaft portion so that the distal end of the fiber element normally projects beyond the free terminal end of the tip portion, and the fiber element is supported in the tip portion and the shaft portion so that it is longitudinally slidable therein along a predetermined path of movement. The sensor portion is adapted so that it communicates with the proximal end of the fiber element for sensing relative longitudinal movement between the fiber element and the tip portion. The shaft portion and the tip portion have a combined length of at least 4½ inches (preferably approximately 6 inches), and the shaft portion is detachable from the sensor portion to permit replacement of the shaft portion, the tip portion and the fiber element. The sensor portion preferably includes an elongated sensor shaft having an aperture in the terminal end thereof, and the shaft portion preferably includes a tubular sleeve which is detachably received on the sensor shaft so that the proximal end of the flexible fiber element extends through the aperture in the sensor shaft and communicates with the sensor portion in the interior of the sensor shaft. The sensor portion preferably further comprises an elongated compressible coil spring in the sensor shaft having a substantially constant compressive force, an optical encoder strip holder in the interior of the coil spring, the encoder strip holder having an encoder strip on one end thereof, and an optical encoder element which is responsive to longitudinal movement of the encoder strip for generating electrical signals which cumulatively correspond to the longitudinal position of the encoder strip relative to the sensor element. The sensor portion is preferably further adapted so that longitudinal movement of the fiber element in the tip portion in a direction toward the sensor portion causes the coil spring in the sensor shaft to be correspondingly compressed while simultaneously causing the encoder strip to be longitudinally repositioned relative to the encoder element. The periodontal probe is preferably constructed so that the shaft portion is rotatable relative to the sensor portion to enable free manipulation of the shaft portion and the tip portion during use of the probe, and the tubular sleeve is preferably detachably snap-received on the sensor shaft. The tip portion is preferably formed in a substantially S-shaped configuration, including oppositely curved inner and outer portions having radii of curvature of between 0.25 inches and 0.75 inches. The fiber element preferably has a length of at least approximately 2 inches, and it is preferably made from a low hydroscopic nylon fiber Further, the fiber element preferably includes a terminal end portion having a series of annular bands thereon of different colors, and the end of the terminal end portion is rounded for ease of entry into the sulcus. The fiber element and the tip portion are preferably adapted so that the terminal end portion of the fiber element normally projects beyond the free terminal end of the tip portion, but so that the terminal end portion retracts into the tip portion as the fiber element is longitudinally advanced in a direction toward the sensor portion. In this regard, since the terminal end portion of the fiber element normally projects beyond the free terminal end of the tip portion, the terminal end portion is not prone to developing a curved or bent "set" which could adversely affect the operation of the probe.

It has been found that the periodontal probe of the instant invention can be effectively and easily utilized for measuring the depths of periodontal pockets in the mouth of a patient in order to monitor the progression of periodontal disease in the patient. In this regard, because the tip portion, the shaft portion and the fiber element are detachable from the sensor portion, they are readily adapted for sanitary disposable constructions; and because the tip portion and the shaft portion preferably have a combined length of at least approximately 4½ inches, they are normally the only portions of the probe which come in contact with the mouth of a patient or the hands of a dentist during a periodontal examination. Accordingly, the risk of transmitting contagious diseases during a periodontal examination is substantially reduced with the periodontal probe of the instant invention. Further, because the shaft portion is rotatable relative to the sensor portion, the shaft portion, the tip portion and the fiber element can normally be freely and effectively manipulated in the mouth of a patient during the course of an examination. The optical encoder provides an effective and reliable means for measuring longitudinal movement of the fiber element, and the compressible coil spring is configured to provide nearly the same resisting force at both extremes of the fiber's travel, resulting in a substantially repeatable correlation between fiber position and resisting force applied to the fiber. Therefore, repeatable measurements are possible as the fiber element is used to probe the depths of periodontal pockets in the mouth of a patient. Further, because the fiber element is preferably made of a low hydroscopic nylon fiber and because it has a length of at least approximately 2 inches, it is generally not possible for saliva to migrate along the length of the fiber element via capillary action to a point where it can contaminate or otherwise adversely affect the sensor portion. Still further, because the tip portion has a series of annular bands thereon of different colors, it is normally possible for an operator of the probe to visually determine the extent by which the fiber element has been inserted into a periodontal pocket during a periodontal examination.

Accordingly, it is a primary object of the instant invention to provide a periodontal probe having a tip portion, a shaft portion and a fiber element which are disposable and readily detachable from a sensor portion of the probe.

Another object of the instant invention is to provide a periodontal probe comprising sequentially disposed, connected sensor, shaft and tip portions and an elongated flexible fiber element in the tip and shaft portions, wherein the shaft portion is rotatable relative to the sensor portion to permit free manipulation of the tip portion during a periodontal examination.

Another object of the instant invention is to provide a periodontal probe comprising sequentially disposed, connected sensor, shaft and tip portions and a fiber element in the tip and shaft portions, wherein the tip portion is formed in an S-shaped configuration to enable the fiber element to slide freely therein.

An even further object of the instant invention is to provide a periodontal probe comprising sequentially disposed, connected sensor, shaft and tip portions and a fiber element in the tip and shaft portions, wherein the fiber element is retractable into the tip portion and wherein the fiber element has a series of different colored annular bands on the terminal end portion thereof to provide a visual indication of the position of the fiber element relative to the gingival margin during a periodontal examination.

Other objects, features and advantages of the invention shall become apparent as the description thereof proceeds when considered in connection with the accompanying illustrative drawings.

DESCRIPTION OF THE DRAWINGS

In the drawings which illustrate the best mode presently contemplated for carrying out the present invention:

FIG. 1 is a perspective view of the periodontal probe of the instant invention;

FIG. 2 is an exploded perspective view thereof;

FIG. 3 is a sectional view of the probe taken along line 3—3 in FIG. 1; and

FIG. 4 is an enlarged sectional view of the terminal end portion of the tip portion of the probe and the fiber element.

DESCRIPTION OF THE INVENTION

Referring now to the drawings, the periodontal probe of the instant invention is illustrated in FIGS. 1-4 and generally indicated at 10 in FIGS. 1-3. The probe 10 comprises sequentially disposed, connected sensor, shaft and tip portions generally indicated at 12, 14 and 16, respectively, and an elongated fiber element generally indicated at 18 which extends through the tip portion 16 and a portion of the shaft portion 14. The probe 10 is operable for probing the gingival tissue around the teeth in the mouth of a patient with the fiber element 18 in order to measure the depths of any periodontal pockets in the gingival tissue. Specifically, in order to measure the depth of a periodontal pocket, the probe 10 is positioned so that the fiber element 18 extends to the bottom of the periodontal pocket and so that the terminal end of the tip portion 16 is located at the intersection between the gum tissue and the exposed lateral surface of the adjacent tooth. When the probe 10 is positioned in this manner, the terminal end portion of the fiber element 18 is normally disposed in a partially retracted position so that the distance by which the terminal end portion of the fiber element 18 projects beyond the tip portion 16 is equal to the depth of the periodontal pocket. In this regard, since the sensor portion 12 is operative for generating electrical signals corresponding to the amount by which the fiber element 18 is retracted into the tip portion 16, the signals generated by the sensor portion 12 can be fed to a suitable signal processing console for easily and accurately calculating the depth of the periodontal pocket.

The sensor portion 12 comprises a pair of mating housing sections 20 and 22, an optical encoder element 24, an elongated encoder strip 26, a tubular sensor shaft 28 having an aperture 30 in the terminal end thereof, an elongated encoder strip holder 32, an elongated coil spring 34, a sensor shaft base 36 and a plastic bearing 38. The encoder element 24 preferably comprises a linear encoder module, such as a Hewlett Packard HEDS-9200-MOO encoder module, which utilizes a high resolution quadrature detection scheme, and it is electrically connected to a signal cord 40 through wires 42 The encoder element 24 includes an open slot or track 44, and it is responsive to movement of the encoder strip 26 through the track 44 for generating an electrical signal each time the encoder strip 26 is advanced by an incremental amount through the track 44. The encoder element 24 is assembled and secured in the housing sections 20 and 22, and a strain-relief collar 46 on the cord 40 is assembled in notches 48 in the housing sections 20 and 22 to prevent the cord 40 from being inadvertently disconnected from the sensor portion 12. When the housing sections 20 and 22 are in assembled relation, they cooperate to define a threaded aperture 49 which is aligned with the track 44. The sensor shaft base 36 is of tubular configuration, and it is received in threaded engagement in the threaded aperture 49. The base 36 includes a tubular neck 50; and the bearing 38, which is preferably made from a suitable low-friction plastic in a tubular configuration, is rotatably received on the neck 50. The bearing 38 has an annular ridge 51 formed thereon as illustrated. The shaft 28 preferably has a length of approximately 2 inches, and it is preferably made from a corrosion-resistant metal, such as stainless steel. The coil spring 34 is preferably made from stainless steel wire having a diameter of approximately 0.010 inches, and it is preferably formed in an approximately ¼ inch O.D. coil which initially has a length of approximately five inches; although, when it is assembled in the shaft 28, it is compressed to a length of approximately 2 inches. It has been found that by constructing and assembling the coil spring 34 in this manner, the coil spring 34 provides a substantially uniform force as it is longitudinally compressed so that it is capable of applying a substantially uniform resistance to longitudinal movement of the fiber element 18 toward the sensor portion 12. The encoder strip 26 is of conventional construction, and it is partially transparent; although it has a plurality of transverse lines thereon which are optically detectable by the encoder element 24 as the encoder strip 26 is passed through the track 44. The holder 32 is preferably made from a suitable plastic material, such as acetal, and it is assembled with the encoder strip 26 so that it is operable for advancing the encoder strip 26 through the track 44. The encoder strip 26 and the holder 32 are assembled in the sensor shaft 28 so that the encoder strip 26 is received in the interior of the coil spring 34, and so that the coil spring 34 biases the holder 32 in a direction away from the encoder element 24. The tubular sensor shaft 28 is assembled with a press fit on the tubular neck 50. When the sensor shaft 28 is assembled on the tubular neck 50 in this manner, the bearing 38, which has an annular ridge 51 thereon, is rotatable on the tubular neck 50 and the encoder strip 26 extends through the base 36 and into the track 44. Accordingly, by moving the encoder holder 32 in the direction of the encoder element 24, the encoder strip 26 is advanced through the track 44 to generate electrical signals in the wires 42, which signals cumulatively provide an indication of the degree to which the encoder strip 26 has been advanced through the track 44.

The shaft portion 14 is of tubular configuration, and it is preferably of approximately 5 inches in length. The shaft portion 14 is preferably integrally molded from a suitable plastic material, and it includes a tubular sleeve portion 52 having a substantially smooth cylindrical outer configuration and a gripping portion 54 of slightly reduced diameter having a series of annular gripping rings thereon. The sleeve portion 52 has a groove ring 56 formed on the inner side thereof adjacent the terminal end of the sleeve portion 52. The groove ring 56 is dimensioned and positioned for snap-receiving the annular ridge 51 on the bearing 38 in order to detachably secure the shaft portion 14 to the sensor portion 12 so that it is rotatable with the bearing 38 relative to the other components of the sensor portion 12.

The tip portion 16 comprises a guide tube generally indicated at 57 which includes first and second halves 58 and 60, respectively, and a corrosion-resistant, stainless steel tip element 62. The guide tube halves 58 and 60 are preferably each integrally molded from a suitable rigid plastic material, and each has an elongated longitudinally extending inner channel 64 formed therein. The halves 58 and 60 are constructed so that when they are assembled together, the channels 64 therein cooperate to define an elongated passage of substantially circular section which extends longitudinally through the guide tube 57, the passage thereby formed having a diameter which is slightly greater than that of the fiber element 18. As illustrated in FIG. 3, the guide tube 57 includes an elongated, substantially straight, guide portion 64, an S-shaped terminal end portion 66, and a flange 68 at the intersection between the guide portion 64 and the terminal end portion 66. The guide portion 64 is received and secured in the gripping portion 54 of the shaft portion 14 so that the flange 68 abuts the outer terminal end of the gripping portion 54. When the tip portion 16 is assembled with the shaft portion 14 in this manner, the passage defined by the channels 64 is substantially aligned with the aperture 30 in the terminal end of the sensor shaft 28, and the terminal end of the guide portion 64 is closely spaced from the terminal end of the sensor shaft 28. The terminal portion 66 is formed in an S-shaped configuration, and it includes oppositely curved inner and outer portions 70 and 72, respectively. The inner portion 70 is constructed so that the sectional dimension thereof is substantially reduced in its extent from the flange 68 to the outer portion 72, and both the inner portion 70 and the outer portion 72 are preferably formed so that they have radii of curvature of between 0.25 inches and 0.75 inches. In this regard, by constructing the terminal portion 66 so that it includes oppositely curved inner and outer portions 70 and 72, respectively, the fiber element 18 must inherently follow an S-shaped path as it is retracted into the tip portion 16. It has been found that by forcing the fiber element 18 to follow an S-shaped path rather than a path which is curved in only one direction, the fiber element 18 slides substantially more easily and freely through the tip portion 16. As a result, the only significant resistance force applied to the fiber element 18 results from the substantially constant resilient resistance of the spring 34 so that the amount of resistance applied to the movement of the fiber element 18 is maintained at a substantially constant predetermined level. Further, the S-shaped configuration of the terminal portion 66 enables the probe 10 to be more easily manipulated in the mouth of a patient to measure the depths of periodontal pockets with the fiber element 18. The tip element 62 is of tubular configuration, and it is received and secured in the guide portion 57 so that it projects beyond the terminal end thereof. The tip element 62 has an internal diameter which is slightly greater than that of the fiber element 18 so that it provides support for the fiber element 18 at the outer end of the tip portion 16 as the fiber element 18 is used to probe the gingival tissue of a patient.

The fiber element 18 is preferably made of a low hydroscopic nylon, such as Tynex (DuPont TM), and it preferably has a diameter of approximately 0.022 inches. The fiber element 18 preferably has a length of at least approximately 2 inches in order to prevent saliva from traveling along the length thereof via capillary action to a point where it can contaminate the sensor portion 12. The fiber element 18 has a proximal end 74 and a distal end portion generally indicated at 76 which terminates in a distal end 78. The distal end portion 76 preferably has a length of approximately 10 millimeters, and it has a series of annular bands 80 of different colors formed thereon. The bands 80 are preferably formed by either surface coloration or sublimation dyes, and they preferably include sequentially disposed green, blue, orange and black bands of 6 millimeters, 2 millimeters, 2 millimeters and 3 millimeters in length, respectively, wherein the black colored band terminates in the distal end 78. In this regard, it has been found that the colored bands 80 on the distal end portion 76 of the fiber element 18 make it possible to visually determine the location of the distal end portion 76 relative to the gingival margin during a periodontal examination. Further, it has been found that the different colored bands 80 are substantially better for this purpose than other types of markings, since the distal end 78 is not normally visible once it has been inserted into a periodontal pocket, and therefore it cannot be used as a visual reference point. In any event, it has been found that by observing the colored bands 80 it is possible to visually determine the extent to which the distal end portion 76 has been advanced into the periodontal pocket. This allows a visual approximate measure of the pocket depth. By thereafter pressing the distal end of the tip 62 to the gingival corona, an electronic representative of the pocket depth is generated by the encoder element 24.

For use and operation of the probe 10, the sensor portion 12 is first electrically connected to a suitable readout and/or recording device for indicating and/or recording the depths of periodontal pockets measured with the probe 10 during a periodontal examination. Thereafter, the probe 10 can be utilized to conduct a periodontal examination by inserting the distal end portion 76 of the fiber element 18 into various periodontal pockets in the mouth of a patient. In this regard, as the fiber element 18 is inserted into a periodontal pocket, the spring 34 applies a substantially uniform compression thereto which resists advancement of the fiber element 18 into the shaft portion 14 in a direction toward the sensor portion 12. However, once the distal end 78 of the fiber element 18 has reached the bottom of a periodontal pocket, a visual determination of pocket depth can be made by observing the positions of the colored bands 80 relative to the gingival margin. Thereafter, the probe is positioned so that the terminal end of the tip element 62 is aligned with the gingival margin, i.e. the point where the gingival tissue meets the lateral surface of the adjacent tooth. Once the probe 10 has been positioned in this manner, the distance by which the distal end portion 76 extends beyond the terminal end of the tip element 62 represents the depth of the periodontal pocket. In this regard, as the distal end portion 76 is retracted into the tip portion 16 to position the terminal end of the tip element 62 at the gingival margin, the encoder strip 26 is moved rearwardly through the encoder element 24 so that electrical signals are generated by the encoder element 24, which signals cumulatively provide an indication of the amount of relative movement which has taken place between the encoder strip 26 and the encoder element 24. Accordingly, the amount by which the distal end portion 76 is retracted into the tip portion 16 can be readily determined from the signals generated by the encoder element 24, and the distance by which the distal end portion 76 extends beyond the terminal end of the tip element 62 can also be readily determined to provide an indication of the depth of the periodontal pocket.

Accordingly, it is seen that the periodontal probe 10 has several specific advantages over the heretofore available devices for measuring periodontal pocket depths. In this regard, the spring 34 provides substantially uniform resilient resistance to movement of the fiber element 18 in a direction toward the sensor portion 12 so that a substantially repeatable level of pressure is applied to the gingival tissue by the distal end 78. The colored bands 80 provide an effective and convenient visual indication of the amount by which the distal end portion 76 has been inserted into a periodontal pocket during a periodontal examination; and because the sensor portion 12 is rotatable relative to the shaft portion 14, the shaft portion 14, the tip portion 16 and the fiber element 18 can be easily manipulated in the mouth of a patient. Further, because the shaft portion 14 is detachable from the sensor portion 12, and because the shaft portion 14, the tip portion 16 and the fiber element 18 are all preferably made from relatively inexpensive plastic materials, the shaft portion 14, the tip portion 16 and the fiber element 18 can be replaced after each periodontal examination to prevent the spread of disease. Still further, because of the overall combined length of the replaceable portions of the probe 10, only the replaceable portions normally come in contact with the mouth of a patient so that the likelihood of transmitting diseases via the probe 10 is even further reduced. In addition, because the probe 10 utilizes an optical encoder element 24 and an encoder strip 26 for measuring movement of the fiber element 18, the probe 10 is effectively operable for generating highly accurate electrical signals which can be utilized to determine the depths of periodontal pockets. Further, because the distal end portion 76 of the fiber element 18 includes the different colored bands 80, visual determinations of pocket depths can also be made in a relatively accurate manner. Still further, because the retractable fiber element 18 normally projects beyond the end of the tip element 62, the distal end portion 76 is not prone to developing a curved "set", and the distal end portion 76 can easily be retracted to a position wherein the distal end 78 is even with the terminal end of the tip element 62 to calibrate the probe 10 prior to use. As a result, for these reasons as well as the other reasons hereinabove set forth, it is seen that the periodontal probe of the instant invention represents a significant advancement which has substantial commercial merit in the dental art.

While there is shown and described herein certain specific structure embodying the invention, it will be manifest to those skilled in the art that various modifications and rearrangements of the parts may be made without departing from the spirit and scope of the underlying inventive concept and that the same is not limited to the particular forms herein shown and described except insofar as indicated by the scope of the appended claims.

What is claimed is:

1. A periodontal probe comprising sequentially disposed, connected sensor, shaft and tip portions, and an elongated flexible fiber element extending longitudinally through said tip portion and at least a portion of said shaft portion, said tip portion terminating in a terminal end, said fiber element having distal and proximal ends and being assembled in said tip portion and said shaft portion so that it normally projects beyond the terminal end of said tip portion terminating in said distal end, said fiber element being supported in said tip portion and said shaft portion so that it is longitudinally slidable therein along a predetermined path of movement, said tip portion and said shaft portion being integrally and permanently connected, the combined length of said tip portion and said shaft portion being at least approximately 4½ inches, said sensor portion communicating with the proximal end of said fiber element for sensing relative longitudinal movement between said fiber element and said tip portion, said shaft portion being detachable from said sensor portion to permit replacement of said shaft portion, said tip portion and said fiber element.

2. In the periodontal probe of claim 1, said shaft portion comprising an elongated tubular sleeve, said sensor portion comprising an elongated tubular sleeve, said sensor portion comprising an elongated sensor shaft, including a terminal end having an aperture therein, said tubular sleeve being detachably received on said sensor shaft, said fiber element extending through said aperture, the proximal end of said fiber element communicating with said sensor portion in the interior of said sensor shaft.

3. In the periodontal probe of claim 1, said shaft portion being rotatable relative to at least a portion of said sensor portion.

4. In the periodontal probe of claim 2, said tubular sleeve being detachably snap received on said sensor shaft.

5. In the periodontal probe of claim 4, said tubular sleeve being rotatable relative to said sensor shaft.

6. In the periodontal probe of claim 1, said sensor portion comprising an optical encoder which is responsive to longitudinal movement of the proximal end of said fiber element for generating electrical signals corresponding to the longitudinal position of said fiber element relative to said tip portion.

7. In the periodontal probe of claim 6, said sensor portion including an elongated compressible coil spring having a substantially constant compressive force, longitudinal movement of said fiber element in a direction toward said sensor portion being resisted by the compressive force of said spring and causing said spring to be compressed.

8. In the periodontal probe of claim 7, said optical encoder including an elongated movable encoder strip and a stationery encoder element, said encoder strip being substantially longitudinally aligned with said spring and communicating with the proximal end of said fiber element so that said encoder strip is longitudinally repositioned relative to said encoder element as said fiber element is longitudinally moved in said tip portion.

9. In the periodontal probe of claim 6, said shaft portion being rotatable relative to said optical encoder.

10. In the periodontal probe of claim 1, the combined length of said tip portion and said shaft portion being approximately 6 inches.

11. In the optical encoder of claim 1, said tip portion including a terminal portion of S-shaped configuration.

12. In the periodontal probe of claim 11, said S-shaped terminal portion including oppositely curved inner and outer portions having radii of curvature of between 0.25 inches and 0.75 inches.

13. In the periodontal probe of claim 1, said fiber element having a length of at least approximately 2 inches.

14. In the periodontal probe of claim 1, said fiber element comprising a low hydroscopic nylon fiber.

15. In the periodontal probe of claim 1, said fiber element including a distal end portion which terminates in said distal end, said distal end portion having a series of annular bands thereon of different colors, said distal end portion normally projecting beyond the free terminal end of said tip portion but retracting into said tip portion as said fiber element is longitudinally advanced toward said sensor portion.

16. In the periodontal probe of claim 1, said tip portion and said shaft portion being made of a plastic material.

17. A periodontal probe comprising sequentially disposed, connected sensor, shaft and tip portions, and an elongated flexible fiber element extending longitudinally through said tip portion and at least a portion of said shaft portion, said tip portion terminating in a terminal end, said fiber element having distal and proximal ends and being assembled in said tip portion and said shaft portion so that it normally projects beyond the free terminal end of said tip portion terminating in said distal end, said fiber element being supported in said tip portion and said shaft portion so that it is longitudinally slidable therein along a predetermined path of movement, said sensor portion communicating with the proximal end of said fiber element for sensing relative longitudinal movement between said fiber element and said tip portion, said shaft portion being freely rotatable relative to at least a portion of said sensor portion without affecting the attachment of said shaft portion to said sensor portion.

* * * * *